United States Patent [19]

Miyashita et al.

[11] 4,308,268
[45] Dec. 29, 1981

[54] MAYTANSINOIDS, PHARMACEUTICAL COMPOSITIONS THEREOF AND METHOD OF USE THEREOF

[75] Inventors: Osamu Miyashita, Osaka; Hiroshi Akimoto, Nishinomiya, both of Japan

[73] Assignee: Takeda Chemical Industries, Ltd., Osaka, Japan

[21] Appl. No.: 153,905

[22] Filed: May 28, 1980

[30] Foreign Application Priority Data

Jun. 11, 1979 [JP] Japan .................................. 54/73790

[51] Int. Cl.³ .................. A61K 31/535; C07D 488/16; C07D 521/00
[52] U.S. Cl. .......................... 424/248.54; 260/239.3 P
[58] Field of Search ................................. 260/239.3 P; 424/248.54

[56] References Cited

U.S. PATENT DOCUMENTS

| | | | |
|---|---|---|---|
| 3,896,111 | 7/1975 | Kupchan et al. | 260/239.3 T |
| 4,137,230 | 1/1979 | Hashimoto et al. | 260/239.3 P |
| 4,162,940 | 7/1979 | Higashide et al. | 260/239.3 P |
| 4,248,870 | 2/1981 | Miyashita et al. | 260/239.3 P |

OTHER PUBLICATIONS

Kupchan et al., "J. Med. Chem." (1978), vol. 21, No. 1, pp. 31-37.

*Primary Examiner*—Robert T. Bond
*Attorney, Agent, or Firm*—Wegner & Bretschneider

[57] ABSTRACT

Novel maytansinoids of the formula:

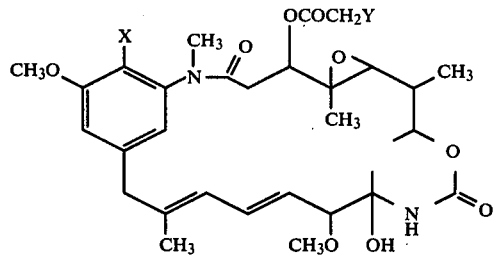

wherein X is H or Cl, and Y is Cl, OH, SH, CN, $NO_2$, —OR or —$S(O)_n$R wherein R is slkyl, aryl, aralkyl or azaheterocyclic group which may be substituted, and n is 0, 1 or 2, have antimitotic, antitumor and antimicrobial activities.

14 Claims, No Drawings

MAYTANSINOIDS, PHARMACEUTICAL COMPOSITIONS THEREOF AND METHOD OF USE THEREOF

This invention relates to novel maytansinoid compounds which are of value as medicines, and to their production and used.

More particularly, this invention relates to compounds of the formula:

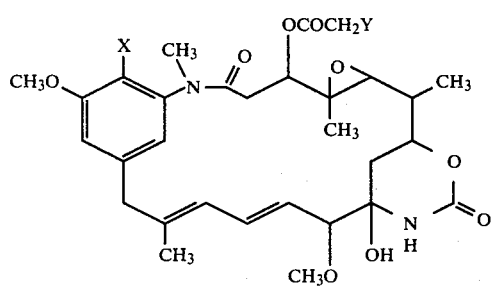

wherein X is H or Cl, and Y is Cl, OH, SH, CN, NO$_2$, —OR or —S(O)$_n$R wherein R is alkyl, aryl, aralkyl or azaheterocyclic group which may be substituted, and n is 0, 1 or 2, and their production.

Referring to the above formula (I), the alkyl designated by R may for example be $C_{1-8}$ alkyl (e.g. methyl, ethyl, propyl, isopropyl, butyl, isobutyl, sec-butyl, tert-butyl, pentyl, hexyl, heptyl or octyl). Preferably, it is $C_{1-4}$ alkyl. As examples of said aryl, there may be mentioned phenyl, α- or β-naphthyl, and preferably phenyl. Said aralkyl may for example be phenyl-$C_{1-4}$ alkyl (e.g. benzyl, α-methylbenzyl or phenethyl). As preferable examples of said azaheterocyclic group, there may be mentioned 5- or 6-membered heterocyclic groups having one to four of N such as 2- or 4-pyridyl, 2- or 4(6)-pyrimidyl, 3(6)-pyridazinyl, 2- or 3-pyrazinyl, 2-s-triazinyl, 2-(1,3,4-triazinyl), 2- or 4(5)-imidazolyl, 3(5)-pyrazolyl, 2-(1,3,4-triazolyl), 5-tetrazolyl, 2-piperazinyl, 2-pyrrolidinyl, 2-oxazolyl, 2-thiazolyl, 2- or 5-oxadiazolyl, 2- or 5-thiadiazolyl, 2-(2-thiazolinyl), 2-benzimidazolyl, 2-benzoxazolyl and 2-benzothiazolyl.

Said alkyl, aryl, aralkyl and azaheterocyclic groups as R may have a substituent or substituents. Examples of said substituents include $C_{1-4}$ alkoxy (e.g. methoxy, ethoxy, propoxy, isopropoxy, n-butoxy, isobutoxy, sec-butoxy, tert-butoxy), $C_{2-4}$ alkanoyl (e.g. acetyl, propionyl, n-butyryl, isobutyryl), $C_{2-4}$ alkanoyloxy (e.g. acetyloxy, propionyloxy, n-butyryloxy, isobutylyloxy), $C_{2-4}$ alkoxycarbonyl (e.g. methoxycarbonyl, ethoxycarbonyl, n-propoxycarbonyl, isopropoxycarbonyl), halogens (e.g. chlorine, fluorine, bromine, iodine), hydroxyl, nitro, cyano, trifluoromethyl, di-$C_{1-4}$ alkylamino (e.g. dimethylamino, diethylamino, dipropylamino, diisopropylamino, dibutylamino), $C_{1-4}$ alkylthio (e.g. methylthio, ethylthio, n-propylthio, isopropylthio, n-butylthio, isobutylthio, sec-butylthio, tert-butylthio), $C_{1-4}$ alkylsulfinyl (e.g. methylsulfinyl), $C_{1-4}$ alkylsulfonyl (e.g. methylsulfonyl), sulfamoyl, mono- or di-$C_{1-4}$ alkylsulfamoyl (e.g. methylsulfamoyl, dimethylsulfamoyl), oxo, thioxo, $C_{1-4}$ alkanoylamino groups (e.g. formylamino, acetylamino, propionylamino, butyrylamino, isobutyrylamino) and $C_{1-4}$ alkylsulfonylamino (e.g. methylsulfonylamino, ethylsulfonylamino). In addition to the above, when R is alkyl, there may be present such substituents as —O(CH$_2$CH$_2$O)$_m$R$^1$ (m is an integer 1 to 4 inclusive, and R$^1$ is methyl or ethyl), and when R is aryl, aralkyl and azaheterocyclic group, there may be present such substituents as $C_{1-4}$ alkyl (e.g. methyl, ethyl, propyl, isopropyl). Among these substituents, when R is alkyl, a preferable substituent is alkoxy, halogen, alkyltho or —O(CH$_2$CH$_2$O)$_m$R$^1$, and when R is aryl and azaheterocyclic group, a preferable substituent is alkoxy, halogen or alkylthio.

A preferred embodiment provides compounds of the formula (I) wherein X is H or Cl, and Y is Cl, OH, SH, CN, NO$_2$, —OR or —S(O)$_n$R, wherein n is 0, 1 or 2, and R is $C_{1-8}$ alkyl, phenyl, naphthyl, phenyl-$C_{1-4}$ alkyl, or 5- or 6-membered azaheterocyclic group having one to four of N, said R group being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, hydroxyl, nitro, cyano, trifluoromethyl, di-$C_{1-4}$ alkylamino, $C_{1-4}$ alkylthio, $C_{1-4}$ alkylsulfinyl, $C_{1-4}$ alkylsulfonyl, sulfamoyl, mono- or di-$C_{1-4}$ alkylsulfamoyl, oxo, thioxo, $C_{1-4}$ alkanoylamino, $C_{1-4}$ alkylsulfonylamino or —O(CH$_2$C-H$_2$O)$_m$R$^1$ wherein R$^1$ is methyl or ethyl and m is an integer 1 to 4 inclusive.

A further preferred embodiment provides compound (I) wherein X is Cl, and Y is Cl, CN, —OR or —S-(O)$_n$R, wherein n is 0,1 or 2, and R is $C_{1-8}$ alkyl, phenyl, phenyl-$C_{1-4}$ alkyl and pyridyl, said groups being unsubstituted or substituted by $C_{1-4}$ alkoxy, halogen, nitro and —O(CH$_2$CH$_2$O)$_m$R$^1$ wherein R$^1$ is methyl or ethyl and m is an integer 1 to 4 inclusive.

The maytansinoid compound (I) of the present invention can be produced by acylating maytansinol or dechloromaytansinol of the formula:

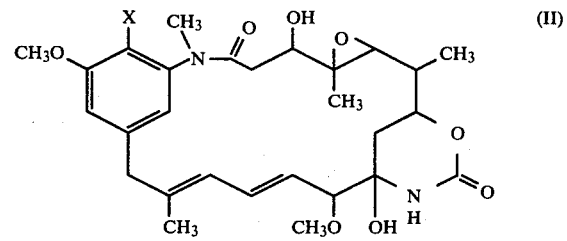

wherein X is as defined above, with a carboxylic acid of the formula:

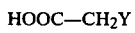

wherein Y is as defined above, or its reactive derivative with respect to the carboxyl function thereof.

An exemplary reaction procedure comprises acylating a compound (II) with a carboxylic acid (III) in the presence of a carbodiimide. Based on compound (II), carboxylic acid (III) may be used in an amount of, for example, about 1 to 50 molar equivalents and, in many cases, is preferably employed in an amount of about 1–15 molar equivalents. The carbodiimide may be used in an amount of about 1 to 70 molar equivalents based on compound (II) and, in many cases, is preferably employed in an amount of about 1–20 molar equivalents. The usable carbodiimide is preferably dicyclohexylcarbodiimide, although such other carbodiimides may also be employed as, for example, diphenylcarbodiimide, di-o-tolylcarbodiimide, di-p-tolylcarbodiimide, di-tert-butylcarbodiimide, 1-cyclohexyl-3-(2-morpholinoethyl)carbodiimie, 1-cyclohexyl-3-(4-diethylaminocyclohexyl)carbodiimide, 1-ethyl-3-(2-diethylaminopropyl)carbodiimide and 1-ethyl-3-(3-dimethyl-aminopropyl)carbodiimide.

This acylation reaction may be carried out in a suitable solvent. Examples of such solvent include esters (e.g. ethyl acetate), ethers (e.g. diethyl ether, dioxane, tetrahydrofuran), halogenated hydrocarbons (e.g. methylene chloride, chloroform), nitriles (e.g. acetonitrile), aromatic hydrocarbons (e.g. benzene), nitromethane, pyridine, dimethylformamide, dimethylsulfoxide, sulfolane, etc., as well as appropriate mixtures of such solvents.

This reaction may be usually carried out at a suitable temperature from ice-cooling to the reflux point of the reaction system.

This acylation reaction can be advantageously hastened with the aid of a catalyst capable of promoting acylation of compound (II). The catalyst may be an appropriate acid or base. The basic catalyst includes, among others, tertiary amine compounds (e.g. aliphatic tertiary amines such as triethylamine; aromatic tertiary amines such as pyridine, $\alpha$-, $\beta$-, or $\gamma$-picoline, 2,6-lutidine, 4-dimethylaminopyridine, 4-(1-pyrrolidinyl)pyridine, dimethylaniline, diethylaniline), halogenated alkali metals (e.g. potassium fluoride, anhydrous lithium iodide), salts of organic acids (e.g. sodium acetate) and so forth. The acid catalyst includes, among others, Lewis acids [e.g. anhydrous zinc chloride, anhydrous aluminum chloride ($AlCl_3$), anhydrous ferric chloride, titanium tetrachloride ($TiCl_4$), stannic tetrachloride ($SnCl_4$), antimony pentachloride, cobalt chloride, cupric chloride, boron trifluoride etherate, etc.], inorganic strong acids (e.g. sulfuric acid, perchloric acid, hydrochloric acid, hydrobromic acid, etc.), organic strong acids (e.g. benzenesulfonic acid, p-toluenesulfonic acid, trifluoroacetic acid, trichloroacetic acid, etc.), acidic ion exchange resins (e.g. polystyrene-sulfonic acid), etc. The catalyst is used in a catalytic amount sufficient to promote acylation, for example, about 0.01 to about 10 molar equivalents, preferably about 0.01 to about 1 equivalent, based on carboxylic acid (III). The use of such a catalyst leads in many cases to remarkably improved yields of maytansinoid compound (I).

In connection with this reaction, when compound (I) having an optically active acyl group is desired, the use of the corresponding optical form of carboxylic acid (III) proves advantageous in some instances.

The acylation process utilizing a reactive derivative of carboxylic acid (III) with respect to its carboxyl function may for example be a process which comprises using a derivative having a functional group capable of acylating the 3-position of compound (II) such as the acid anhydride of carboxylic acid (III). The solvent and catalyst for use in this acylation reaction may be the same as those mentioned hereinbefore in connection with acylation in the presence of a carbodiimide. The reaction temperature may usually range from about $-20°$ C. to about $+100°$ C. and preferably about $20°$ C. to about $40°$ C. The reaction may be hastened by heating the reaction system to a still higher temperature.

In the above-mentioned acylation, when a sensitive group to acylation (e.g. hydroxyl, mercapto, amino, carboxyl) exists in carboxylic acid (III), said group may be protected in advance by a suitable protective group known per se (e.g. tert-butoxycarbonyl, trifluoroacetyl, phenol ester, lower alkyl ester).

A compound (I) wherein Y is —OR or —SR may be produced by reacting a compound (I) wherein Y is chlorine (or other halogen) with ROH, RSH or a metal sat thereof (e.g. sodium salt, potassium salt, lithium salt, calcium salt, magnesium salt). When ROH or RSH itself is used as the reaction component, the reaction is carried out in the presence of a base. As examples of said base, there may be mentioned alkali metal hydroxides (e.g. sodium hydroxide, potassium hydroxide) alkali metal carbonates (e.g. sodium carbonate, potassium carbonate), tertiary amines (e.g. triethylamine, pyridine, $\alpha$-, $\beta$- or $\gamma$-picoline, 2,6-lutidine, 4-dimethyl aminopyridine, 4-pyrrolidinopyridine, dimethylaniline, diethylaniline). This reaction may be carried out in a suitable solvent. Examples of such solvent include esters (e.g. ethyl acetate), ethers (e.g. diethyl ether, dioxane, tetrahydrofuran), halogenated hydrocarbons (e.g. dichloromethane, chloroform), nitriles (e.g. acetonitrile), aromatic hydrocarbons (e.g. benzene, toluene), nitromethane, pyridine, dimethylformamide, dimethylsulfoxide and sulfolane as well as appropriate mixtures of such solvents.

This reaction may also be carried out in a homogeneous mixture of said solvent and water or in a two-phase-system from an organic layer and an aqueous layer. In the latter case, it may be desirable to employ a phase-transfer catalyst (e.g. tetraethylammonium hydroxide, benzyl trimethylammonium bromide, benzyl triethylammonium iodide, cetyl trimethylammonium chloride or bromide). This reaction may be carried out at a suitable temperature, normally from $0°$ C. to the reflux point of the reaction system.

ROH, RSH or its metal salt may be used in an amount of 1–100, preferably 1–30 molar equivalents to the starting compound (I). The phase-transfer catalyst may be used in 0.1–10, preferaby 1–5 molar equivalents. A compound (I) wherein Y is —SOR or —$SO_2R$ may be produced by oxidizing a compound (I) wherein Y is —SR with a suitable oxidizing agent such as hydrogen peroxide, peroxy acid (e.g. peracetic acid, pertrifluoroacetic acid, perbenzoic acid, permetachlorobenzoic acid), periodate (e.g. sodium salt) or permanganate (e.g. sodium or potassium salt).

The maytansinoid compound (I) thus produced by the above-mentioned procedures can be isolated by subjecting the reaction mixture to a conventional procedure such as concentration, solvent extraction, chromatography, recrystallization, etc. When compound (I) is produced as a mixture of isomers (e.g. D- and L-isomers), the isomers can be separated from each other generally by a conventional procedure, e.g. silica gel column chromatography. The maytansinoid compound (I) according to this invention includes such individual isomers and all mixtures of the isomers.

The maytansinoid compound (I) according to this invention has strong antimitotic and antitumor activities with comparatively low toxicity and are therefore suited for administration, oral or parenterally, to tumor-bearing warm-blooded animals (e.g. mouse, rat, rabbit, dog, cat and man) for the purpose of prolonging their survival times. Each compound (I) is normally administered in the form of a pharmaceutical preparation (e.g. injectable solution) as formulated with a carrier, diluent or the like which is known per se.

When compound (I) is administered in the form of an injectable preparation, it may be given subcutaneously, intraperitoneally, intravenously or intramuscularly, for instance. The dosage of compound (I) varies with the kind, symptom, administration route, etc. but, for example, in case of intravenous administration for prolonging life span of the animal suffering from leukemia or melanoma, it may be decided from the range of about 1 to 1000 μg/kg body weight, preferably about 10 to 500 μg/kg body weight, especially about 10 to 250 μg/kg body weight, per dose.

The injectable preparation can be prepared by the established pharmaceutical procedure; for example by dissolving about 50 μg to 3 mg of compound (I) in each about 0.5 ml of alcohol (e.g. ethanol), followed by addition of a sufficient amount of physiological saline to make a total of 10 ml. When a small dosage is indicated, the above solution may be further diluted with physiological saline.

The maytansinoid compounds (I) according to this invention are of value also in that they have antimicrobial activity, e.g. antifungal and antiprotazal properties. Thus, for example, the maytansinoid compounds (I) are useful for treating *Tetrahymena pyriformis* W. As an antifungal or antiprotozoal agent, compound (I) is instrumental in assays of the bacterial flora of soil, active sludge, animal body fluids, etc. Thus, for the isolation of useful bacteria from soil samples or in the assay of activity of bacteria to the exclusion of those of protozoa and fungi in connection with the operation and analysis of active sludge systems for waste water treatment, the compound (I) can be advantageously employed to ensure selective growth of bacteria without permitting growth of the concomitant protozoa and fungi. Thus, such a sample is added to a liquid or solid medium, and per milliliter of the inoculated medium, 0.1 ml of a 1% methanol-water solution of about 10 to 100 μg/ml of compound (I) is added, and then incubated to let the bacteria grow and multiply.

The maytansinoid compound (I), in an amount of 0.02 ml of a 1 mg/ml aqueous solution, is able to inhibit growth of causative microorganisms of stem rot, helminthosporium leaf rot and sheath blight in rice plants, for instance, and can therefore be used for the treatment of such plant diseases. The procedure may comprise dissolving compound (I) in 1% aqueous methanol to a concentration of about 0.5 to 5 μg/ml and spraying rice plants with the solution.

The following reference example and working examples are intended to describe this invention in further detail and not to limit its scope. In these examples, Rf values are measured by the thin-layer chromatography on a precoated silica-gel plate (Merck, HPTLC).

REFERENCE EXAMPLE 1

In 800 ml of dry tetrahydrofuran (THF) is dissolved 15.0 g of antibiotic Ansamitocin mixture (12% of ansamitocin P-2, 71% of P-3 and 17% of P-4) and under dry nitrogen gas streams, the solution is cooled to −50° C. in a dry ice-acetone bath. Then, 13.0 g of lithium aluminum hydride (LAH) is added in a single dose and the mixture is stirred at −50° C. to −22° C. for 2 hours. Then, at −28° C., a further 3 g of LAH is added and the reaction mixture is stirred at −28° C. to −22° C. for 80 minutes. Thereafter, at −50° C., 750 ml of 2 N HCl is added dropwise with caution and the reaction mixture is extracted three times with 2.6 l, 1.6 l and 0.8 l portions of ethyl acetate. The extracts are pooled, washed with a saturated aqueous solution of sodium chloride (100 ml×2) and dried (MgSO$_4$, 250 g). The solvent is distilled off under reduced pressure and the residue (13.6 g) is chromatographed on a column of silica gel (1.2 kg), elution being carried out with ethyl acetate-water (98.5:1.5, V/V). The eluate is collected in 400-gram fractions. Fractions 35 through 52 are pooled, the solvent distilled off and the residue dried in vacuo to obtain 7.25 g of maytansinol. Then, fractions 53 through 68 are similarly treated to obtain 1.55 g of a substantially equimolar mixture of maytansinol and dechloromaytansinol. Similarly, fractions 69 through 86 yield 0.78 g of dechloromaytansinol.

This product is reprecipitated from chloroform-hexane to obtain 0.71 g of dechloromaytansinol.

m.p. 174°–179° C. (decompn.).

Mass spectrum (m/e): 469, etc.

UV spectrum ($\lambda_{max}^{MeOH}$) nm: 231.5, 241.5, 250.5, 277.5, 286.

EXAMPLE 1

In 4.5 ml of dichloromethane are dissolved 130 mg of maytansinol, 238 mg of dicyclohexylcarbodiimide (DCC), 109 mg of monochloroacetic acid and 56 mg of p-dimethylaminopyridine (DMAP). The mixture is stirred at room temperature for 3 hours, and the insolubles are filtered off. The solvent is then distilled off under reduced pressure and the residue purified by silica-gel column chromatography to yield 139 mg of maytansinol 3-monochloroacetate.

Rf=0.59 (developing solvent: chloroform-methanol=95:1).

Mass spectrum (m/e): 640(M$^+$), 597(M$^+$−43), 579(M$^+$−61)

EXAMPLE 2

In 4.2 mg of dichloromethane are dissolved 120 mg of maytansinol, 242 mg of 2-(2-ethoxyethoxy) ethoxyacetate, 260 mg of DCC and 51 mg of DMAP. The mixture is stirred at room temperature for an hour, and then, the insolubles are filtered off. The filtrate is concentrated to dryness and the residue purified by silica-gel column chromatography to yield 96 mg of maytansinol 3-[2-(2-ethoxyethoxy)ethoxy]acetate.

Rf=0.66 (developing solvent: chloroform-methanol=90:10).

Mass spectrum (m/e): 738(M$^+$), 677(M$^+$-61)

EXAMPLE 3

In 5.2 ml of dichloromethane is dissolved 146 mg of maytansinol, and to this solution, under stirring at room temperature, 218 mg of phenylacetic acid, 63.4 mg of DMAP and 268 mg of DCC are added. The mixture is allowed to stand at room temperature for 3 hours, then, the insolubles are filtered off and the filtrate is purified by silica-gel column chromatography to yield 119 mg of maytansinol 3-phenylthioacetate.

Rf=0.54 (developing solvent: chloroform-methanol=95:5).

Mass spectrum (m/e): 714(M$^+$), 653(M$^+$-61).

EXAMPLE 4

In 22 ml of methanol is dissolved 79 mg of the maytansinol 3-phenylthioacetate prepared as in Example 3, and to this solution, under stirring at room temperature, a solution of 118 mg of sodium periodate in 22 ml of water is added. The reaction mixture is allowed to stand overnight, and then most of the methanol is distilled off under reduced pressure and the residual aqueous solution extracted with ethyl acetate. The extract is concentrated under reduced pressure to obtain 72 mg of maytansinol 3-phenylsulfinylacetate as crystals.

Rf=0.38 (developing solvent: chloroform-methanol=95:5).
Mass spectrum (m/e): 669(M+-61)

EXAMPLE 5

In 11.4 ml of dichloromethane are dissolved 321 mg of maytansinol, 139 mg of DMAP, 587 mg of DCC and 524 mg of phenylsulfinylacetic acid and the solution is stirred under ice-cooling for 30 minutes. Then, 587 mg of DCC and 524 mg of pheylsulfinylacetic acid are further added. After 2 hours, the insolubles are filtered off and the filtrate is diluted with chloroform, washed with 1 N-hydrochloric acid and a saturated aqueous solution of sodium bicarbonate and concentrated to dryness. The residue is purified by silica-gel column chromatography to yields 72 mg of maytansinol 3-phenylsulfinylacetate.

EXAMPLE 6

In 9.2 ml of methanol is dissolved 96 mg of the maytansinol 3-phenylsulfinylacetate prepared as in Example 4, and to this solution, under stirring at room temperature, a solution of 920 mg sodium periodate in 9.2 ml of water is added. The mixture is allowed to stand for 7 days. The insolubles are filtered off, the filtrate is concentrated to dryness under reduced pressure and the residue is purified by silica-gel column chromatography to yield 31 mg of maytansinol 3-phenylsulfonylacetate.
Rf=0.53 (developing solvent: chloroform-methanol=95:5).
Mass spectrum (m/e): 746(M+), 685(M+-61).

EXAMPLE 7

The maytansinol -monochloroacetate (12.8 mg) prepared according to Example 1 and 4-mercaptopyridine (22.2 mg) are dissolved in 1.0 ml of methanol and to this, in a nitrogen stream, 0.1 ml of 1 N-NaOH is added. The mixture is allowed to stand at room temperature for 6 hours, and then neutralized with 0.1 ml of 1 N-HCl. The solvent is distilled off under reduced pressure and the residue is purified by silica-gel column chromatography to yield 10 mg of maytansinol 3-(4-pyridyl)thioacetate.
Rf=0.27 (developing solvent: chloroform-methanol=95:5).
Mass spectrum (m/e): 715(M+), 654(M+-61).

EXAMPLE 8

In 10 ml of dichloromethane are dissolved 282 mg of maytansinol, 515 mg of DCC and 122 mg of DMAP. Then, a solution (10 ml) of 423 mg 4-pyridylthioacetic acid in dimethylformamide is added and the mixture is stirred at room temperature for 3 days. The insolubles are filtered off and the filtrate is diluted with ethyl acetate and washed with 0.2 N-NaOH. The organic layer is concentrated to dryness under reduced pressure and the residue is purified by silica-gel column chromatography to yield 8.0 mg of maytansinol 3-(4-pyridyl)thioacetate.

EXAMPLE 9

To 10 ml of dry dichloromethane are added 102.7 mg of maytansinol, 154.7 mg of phenoxyacetic anhydride, 207 mg of DCC and 46.6 mg of DMAP and the mixture is stirred at room temperature for 2 hours. The solvent is then distilled off under reduced pressure, the residue dissolved in ethyl acetate and the insolubles are filtered off. The filtrate is dried over $Na_2SO_4$, the solvent distilled off and the residue is subjected to silica-gel chromatography ($SiO_2$, 75 g; solvent=ethyl acetate), the eluate being collected in 15-g fractions. Fractions 14 through 30 are combined, the solvent is distilled off and the residue dissolved in hot ethyl acetate and, then, the solution allowed to cool, whereupon crystals separate out. To this is added ether, and the crystals are recovered by filtration to yield 62.4 mg of maytansinol 3-phenoxyacetate.
m.p. 175°–177° C. (decompn.).
Mass spectrum (m/e): 637(M+-61), 622(M+-76)

EXAMPLE 10

In 5 ml of dry dichloromethane are dissolved 111.5 mg of maytansinol, 275.5 mg of p-bromophenoxyacetic acid and 284.5 mg of DCC, and the solution is stirred at room temperature. After about 10 minutes 48 mg of DMAP is added and the mixture is stirred at room temperature for 30 minutes. The insolubles are then filtered off, the filtrate is concentrated under reduced pressure and the residue is dissolved in ethyl acetate, washed with 1 N-HCl, saturated aqueous sodium bicarbonate and water in that order and dried over $Na_2SO_4$. The solvent is distilled off and the residue is chromatographed on silica gel ($SiO_2$, 45 g; developing solvent: ethyl acetate, ca. 50 ml, then ethyl acetate/ethyl acetate saturated with water=5:1, v/v), the eluate being collected in 15-g fractions. Fractions 8 through 17 are combined and the solvent is distilled off to yield 108.0 mg of maytansinol 3-(p-bromophenoxy)acetate.
m.p. 190°–191° C. (decompn.).
Mass spectrum (m/e): 717 715(M+-61).

EXAMPLE 11

As in Example 10, 114.3 mg of maytansinol, 228 mg of p-chlorophenoxyacetic acid, 295 mg of DCC and 52 mg of DMAP are reacted in 5 ml of dry dichloromethane. The reaction mixture is then worked up and chromatographed in a manner similar to that in Example 10 to yield 105.2 mg of maytansinol 3-(p-chlorophenoxy)acetate from Fractions 10 through 23.
m.p. 186°–187° C. (decompn.).
Mass spectrum (m/e): 673 671 (M+-61).

EXAMPLE 12

As in Example 10, 102.5 mg of maytansinol, 203.6 mg of o-chlorophenoxyacetic acid, 264 mg of DCC and 47 mg of DMAP are reacted, worked up and chromatographed. Fractions 9 through 17 yield 101.8 mg of maytansinol 3-(o-chlorophenoxy)acetate.
m.p. 172°–176° C.
Mass spectrum (m/e): 673 671 (M+-61).

EXAMPLE 13

In a manner similar to that in Example 10, 104.9 mg of maytansinol, 220 mg of p-nitrophenoxyacetic acid, 268 mg of DCC and 45.3 mg of DMAP are made to react, worked up and chromatographed. Fractions 10 through 20 yield 101.7 mg of maytansinol 3-(p-nitrophenoxy)acetate.
Thin-layer chromatography; (solvent: ethyl acetate).
Rf=0.50.
Mass spectrum (m/e): 682(M+-61).

EXAMPLE 14

In a manner similar to that in Example 10, 99.2 mg of maytansinol, 192 mg of m-methoxyphenoxyacetic acid, 253 mg of DCC and 42.8 mg of DMAP are made to react, worked up and chromatographed. Fractions 10 through 17 yield 86.5 mg of maytansinol 3-(m-methoxyphenoxy)acetate.
m.p. 170°-172° C. (decompn.)
Mass spectrum (m/e): 667(M+-61).

EXAMPLE 15

In a manner similar to that in Example 10, 99 mg of maytansinol, 191.3 mg of p-methoxyphenoxyacetic acid, 252.6 mg of DCC and 43 mg of DMAP are made to react, worked up and chromatographed. Fractions 10 through 18 yield 81 mg of maytansinol 3-(p-methoxyphenoxy)acetate.
Mass spectrum (m/e): 667(M+-61)

EXAMPLE 16

In 10 ml of dry acetonitrile are dissolved 104 mg of maytansinol, 50 mg of cyanoacetic acid, 150 mg of DCC and 45 mg of DMAP and the solution is stirred at room temperature for 3 hours. Then, 50 mg of cyanoacetic acid, 115 mg of DC and 25 mg of DMAP are further added and the solution is stirred for 3 days. The insolubles are filtered off, the filtrate is concentrated to dryness under reduced pressure and the residue subjected to silica-gel chromatography (SiO$_2$, 55 g; developing solvent: chloroform-methanol=70:1 to 20:1, v/v), the eluate being collected in 25-g fractions. Fractions 43 through 58 are combined, the solvent is distilled off and the residue is subjected again to silica gel chromatography (SiO$_2$, 40 g; developing solvent; chloroform-methanol=50:1, v/v), the eluate being collected in 20-g fractions. Fractions 21 through 32 are combined and the solvent is distilled off. The above procedure yields 12 mg of maytansinol 3-cyanoacetate.
Mass spectrum (m/e): 570(M+-61).

EXAMPLE 17

In 5 ml of dry dichloromethane are dissolved 66.8 mg of dechloromaytansinol, 215.5 mg of monochloroacetic anhydride, 182 mg of DCC and 92.2 mg of DMAP, and the solution is stirred at room temperature for 30 minutes. The insolubles are filtered off, the filtrate is concentrated to dryness under reduced pressure and the residue washed with 1 N-HCl, saturated aqueous sodium bicarbonate and water in that order and dried over Na$_2$SO$_4$. The solvent is then distilled off and the residue is subjected to silica gel chromatography (SiO$_2$, 40 g; developing solvent: ethyl acetate:ethyl acetate saturated with water=6:1, v/v), the eluate being collected in 15-g fractions. Fractions 10 through 21 are combined and the solvent is distilled off to yield 54.0 mg of dechloromaytansinol 3-chloroacetate.
m.p. 205°-207° C. (decompn.; not liquefied up to 262° C.).
Mass spectrum (m/e): 606(M+), 545(M+-61).

EXAMPLE 18

As in Example 10, 102.3 mg of maytansinol, 181.7 mg of benzyloxyacetic acid, 261.4 mg of DCC and 44.6 mg of DMAP are made to react worked up and chromatographed. Fractions 10 through 17 yield 96.2 mg of maytansinol 3-benzyloxyacetate.
Mass spectrum (m/e): 651(M+-61).

EXPERIMENTAL DATA

Antitumor activity
Therapeutic tests were carried out in mice according to NCI-protocol 1,300, Cancer Cheomther, Reports, Part 3, 1972, Vol. 3, No. 2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C %) |
| --- | --- | --- |
| Maytansinol | 100 | 182 |
|  | 50 | 199 |
|  | 25 | 176 |
| 3-phenoxyacetate | 12.5 | 188 |
| Maytansinol | 400 | 185 |
|  | 200 | 181 |
| 3-phenylthioacetate | 100 | 198 |
|  | 50 | 160 |

Antiprotozoal activity
Antiprotozoal activity of compound (I) was assayed with *Tetrahymena pyriformis* W as the test organism and a medium composed of 20 g tryptose-peptone (Difco Co.), 1 g yeast extract, 2 g glucose, 1000 ml distilled water, 10 ml 1 M phosphate buffer (pH 7.0) as the assay medium. The microorganism was incubated at 28° C. for 44 to 48 hours and the growth inhibitory activity of compound (I) was assayed by the serial dilution method. The minimal inhibitory concentrations of compound (I) are shown in Table 2.

TABLE 2

| Compound | Antiprotozoal activity MIC (μg/ml) *Tetrahymena pyriformis* W |
| --- | --- |
| Maytansinol 3-phenoxyacetate | ≦1 |
| Maytansinol 3-p-chlorophenoxyacetate | ≦1 |
| Maytansinol 3-o-chlorophenoxyacetate | ≦1 |
| Maytansinol 3-p-bromophenoxyacetate | 4 |
| Maytansinol 3-m-methoxyphenoxyacetate | 1-2 |
| Maytansinol 3-phenylthioacetate | 1-2 |

EXAMPLES OF PHARMACEUTICAL COMPOSITIONS

Example A

Composition for Injection
(1) Maytansinol 3-phenoxyacetate: 50 mg;
(2) Ethanol: 10 g;
(3) Polysorbate 80 (Tween 80): 40 g;
(4) Mannitol: 20 g;
(5) Distilled water, a sufficient quantity to make: 1000 ml.

Preparation
(1) is dissolved in (2). To this solution, (3) and (4) are added, followed by the addition of sterilized distilled water to make 1000 ml of the solution. Ten milliliter each of the solution is used to fill 100 amber ampoules and the air within the ampoules is replaced with nitrogen gas, then the ampoule is sealed. All the processes are conducted under sterile conditions.

Example B

Composition for Injection
(1) Maytansinol 3-phenylthioacetate: 100 mg;
(2) Ethanol: 5 g;

(3) Polysorbate 80 (Tween 80): 100 g;
(4) Mannitol: 20 g;
(5) Distilled water, a sufficient quantity to make: 1000 ml.

Preparation

By a similar procedure to that of Example A, an injectable solution of (1) is prepared.

What we claim is:

1. A compound of the formula:

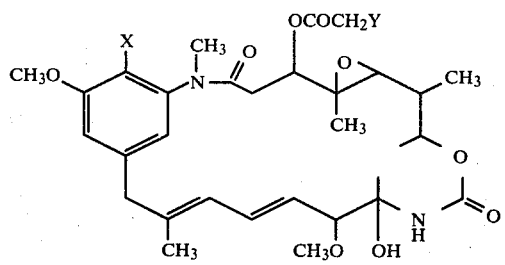

wherein X is H or Cl, and Y is Cl, OH, SH, CN, NO$_2$, —OR or —S(O)$_n$R,
  wherein n is 0, 1 or 2, and
  R is C$_{1-8}$ alkyl, phenyl, naphthyl, phenyl-C$_{1-4}$ alkyl, 2- or 4-pyridyl, 2- or 4(6)-pyrimidyl, 3(6)-pyridazinyl, 2- or 3-pyrazinyl, 2-s-triazinyl, 2-(1,3,4-triazinyl), 2- or 4(5)-imidazolyl, 3(5)-pyrazolyl, 2-(1,3,4-triazolyl), 5-tetrazolyl, 2-piperazinyl, 2-pyrrolidinyl, 2-oxazolyl, 2-thiazolyl, 2- or 5-oxadiazolyl, 2- or 5-thiadiazolyl, 2-(2-thiazolinyl), 2-benzimidazolyl, 2-benzoxazolyl or 2-benzothiazolyl,
  said R group being unsubstituted or substituted by C$_{1-4}$ alkyl, C$_{1-4}$ alkoxy, C$_{2-4}$ alkanoyl, C$_{2-4}$ alkanoyloxy, C$_{2-4}$ alkoxycarbonyl, halogen, hydroxyl, nitro, cyano, trifluoromethyl, di-C$_{1-4}$ alkylamino, C$_{1-4}$ alkylthio, C$_{1-4}$ alkylsulfinyl, C$_{1-4}$ alkylsulfonyl, sulfamoyl, mono- or di-C$_{1-4}$ alkylsulfamoyl, oxo, thioxo, C$_{1-4}$ alkanoylamino, C$_{1-4}$ alkylsulfonylamino or —O(CH$_2$CH$_2$O)$_m$R$^1$ wherein R$^1$ is methyl or ethyl and m is an integer 1 to 4 inclusive.

2. A compound according to claim 1, wherein X is Cl.

3. A compound according to claim 1, wherein the 5- or 6-membered azaheterocyclic group having one to four of N is 2-oxazolyl, 2-thiazolyl, 2- or 4-pyridyl, 2-pyrimidyl or 2-benzimidazolyl.

4. A compound according to claim 1 or 2, wherein Y is Cl, Cn, —OR or —S(O)$_n$R, wherein n is 0, 1 or 2, and R is C$_{1-8}$ alkyl, phenyl, phenyl-C$_{1-4}$ alkyl or pyridyl, said R group being unsubstituted or substituted by C$_{1-4}$ alkoxy, halogen, nitro and —O(CH$_2$CH$_2$O)$_m$R$^1$ wherein R$^1$ is methyl or ethyl and m is an integer 1 to 4 inclusive.

5. A compound according to claim 4, wherein Y is Cl, —OR or —S(O)$_n$R, wherein n is 0, 1 or 2, and R is C$_{1-8}$ alkyl, phenyl, benzyl, phenylethyl or pyridyl, said R group being unsubstituted or substituted by C$_{1-4}$ alkoxy or halogen.

6. A compound according to claim 5, wherein Y is —OR or —SR, wherein R is phenyl or benzyl, said R group being unsubstituted or substituted by C$_{1-4}$ alkoxy or halogen.

7. The compound according to claim 1, which is maytansinol 3-chloroacetate.

8. The compound according to claim 1, which is maytansinol 3-phenoxyacetate.

9. The compound according to claim 1, which is maytansinol 3-o-chlorophenoxyacetate.

10. The compound according to claim 1, which is maytansinol 3-o-methoxyphenoxyacetate.

11. The compound according to claim 1, which is maytansinol 3-p-methoxyphenoxyacetate.

12. The compound according to claim 1, which is maytansinol 3-phenylthioacetate.

13. An antitumor composition which comprises as an active ingredient an effective amount of a compound of the formula:

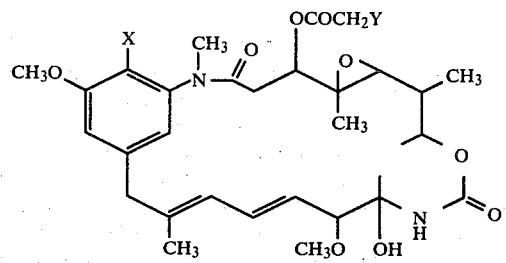

wherein X is H or Cl, and Y is Cl, OH, SH, CN, NO$_2$, —OR or —S(O)$_n$R,
  wherein n is 0, 1 or 2, and
  R is C$_{1-8}$ alkyl, phenyl, naphthyl, phenyl-C$_{1-4}$ alkyl, 2- or 4-pyridyl, 2- or 4(6)-pyrimidyl, 3(6)-pyridazinyl, 2- or 3-pyrazinyl, 2-s-triazinyl, 2-(1,3,4-triazinyl), 2- or 4(5)-imidazolyl, 3(5)-pyrazolyl, 2-(1,3,4-triazolyl), 5-tetrazolyl, 2-piperzinyl, 2-pyrrolidinyl, 2-oxazolyl, 2-thiazolyl, 2- or 5-oxadiazolyl, 2- or 5-thiadiazolyl, 2-(2-thiazolinyl), 2-benzimidazolyl, 2-benzoxazolyl or 2-benzothiazolyl,
  said R group being unsubstituted or substituted by C$_{1-4}$ alkyl, C$_{1-4}$ alkoxy, C$_{2-4}$ alkanoyl, C$_{2-4}$ alkanoyloxy, C$_{2-4}$ alkoxycarbonyl, halogen, hydroxyl, nitro, cyano, trifluoromethyl, di-C$_{1-4}$ alkylamino, C$_{1-4}$ alkylthio, C$_{1-4}$ alkylsulfinyl, C$_{1-4}$ alkylsulfonyl, sulfamoyl, mono- or di-C$_{1-4}$ alkylsulfamoyl, oxo, thioxo, C$_{1-4}$ alkanoylamino, C$_{1-4}$ alkylsulfonylamino or —O(CH$_2$CH$_2$O)$_m$R$^1$ wherein R$^1$ is methyl or ethyl and m is an integer 1 to 4 inclusive,
  and a pharmaceutically acceptable carrier or diluent therefor.

14. A method for inhibiting the growth of tumor cells and prolonging the survival time of a tumor-bearing warm-blooded animal, which comprises administering to said animal an effective amount of a compound of the formula:

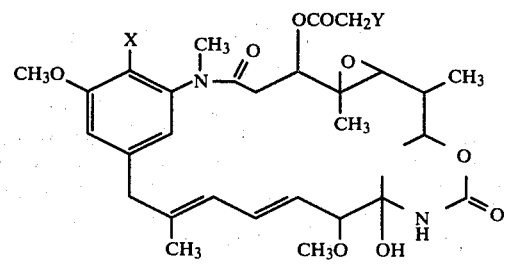

wherein X is H or Cl, and Y is Cl, OH, SH, CN, NO$_2$, —OR or —S(O)$_n$R,
  wherein n is 0, 1 or 2, and
  R is C$_{1-8}$ alkyl, phenyl, naphthyl, phenyl-C$_{1-4}$ alkyl, 2- or 4-pyridyl, 2- or 4(6)-pyrimidyl, 3(6)-pyridazinyl, 2- or 3-pyrazinyl, 2-s-triazinyl, 2-(1,3,4-triazinyl), 2- or 4(5)-imidazolyl, 3(5)-pyrazolyl, 2-(1,3,4-triazolyl), 5-tetrazolyl, 2-piperazinyl, 2-pyrrolidinyl, 2-oxazolyl, 2-thiazolyl, 2- or 5-oxadiazolyl, 2- or 5-thiadiazolyl, 2-(2-thiazolinyl, 2-benzimidazolyl, 2-benzoxazolyl or 2-benzothiazolyl, said R group being unsubstituted or substituted by $C_{1-4}$ alkyl, $C_{1-4}$ alkoxy, $C_{2-4}$ alkanoyl, $C_{2-4}$ alkanoyloxy, $C_{2-4}$ alkoxycarbonyl, halogen, hydroxyl, nitro, cyano, trifluoromethyl, di-$C_{1-4}$ alkylamino, $C_{1-4}$ alkylthio, $C_{1-4}$ alkylsulfinyl, $C_{1-4}$ alkylsulfonyl, sulfamoyl, mono- or di-$C_{1-4}$ alkylsulfamoyl, oxo, thioxo, $C_{1-4}$ alkanoylamino, $C_{1-4}$ alkylsulfonylamino or —O(CH$_2$CH$_2$O)$_m$R$^1$ wherein R$^1$ is methyl or ethyl and m is an integer 1 to 4 inclusive.

* * * * *